US005792609A

United States Patent [19]
Wataya et al.

[11] Patent Number: 5,792,609
[45] Date of Patent: Aug. 11, 1998

[54] DETECTION OF MALARIA

[75] Inventors: Yusuke Wataya, Okayama; Akio Yamane, Hiroshima, both of Japan

[73] Assignee: Wakunaga Pharmaceutical Co., Ltd., Osaka, Japan

[21] Appl. No.: 513,846

[22] PCT Filed: Feb. 28, 1994

[86] PCT No.: PCT/JP94/00324

§ 371 Date: Sep. 11, 1995

§ 102(e) Date: Sep. 11, 1995

[87] PCT Pub. No.: WO94/20613

PCT Pub. Date: Sep. 15, 1994

[30] Foreign Application Priority Data

Mar. 12, 1993 [JP] Japan ................... 5-052541

[51] Int. Cl.$^6$ .................. C12Q 1/68; C12P 19/34; C07H 21/04
[52] U.S. Cl. ............ 435/6; 435/91.2; 536/23.7; 536/24.31; 536/24.33; 935/8; 935/78
[58] Field of Search .............. 435/6, 91.2; 536/23.7, 536/24.31, 24.33; 935/8, 48

[56] References Cited

FOREIGN PATENT DOCUMENTS

| 2 242 904 | 10/1991 | United Kingdom. |
| 8803957 | 6/1988 | WIPO. |
| WO 91/08293 | 6/1991 | WIPO. |

OTHER PUBLICATIONS

Waters et al, Lancet (1989) i, 1343–1346.
Waters et al. Nucleic Acid Research (1989) 17 (No. 5) 2135.
McCutchar, Computer Printout of N–Genesef Accession No's: Q12367–Q12378.
Snounou et al, Molecular & Biochemical Parasitology (Apr. 1993) 58: 283–292.
Li et al, Experimental Parasitology (Feb. 1993) 76: 32–38.
Lal et al, Molecular & Biochemical Parasitology (1989) 36:67–72.
Goman et al, Molecular & Biochemical Parasitology (1991) 45:281–288.
Andrew P. Waters et al., "Rapid, Sensitive Diagnosis of Malaria Based on Ribosomal RNA", The Lancet, vol. I, No. 8651, Jun. 17, 1989.
Database WPI, Section Ch, Week 9340, Derwent Publications Ltd., "Detection of Malaria Parasites Using Primer Selected From 8 Specified Nucleic Acid Fragments", and JP 05 227 998 A, Sep. 7, 1993.

*Primary Examiner*—Carla J. Myers
*Attorney, Agent, or Firm*—Oblon, Spivak, McClelland, Maier & Neustadt, P.C.

[57] ABSTRACT

A method of detecting falciparum, tertian, quartan and ovale malaria parasites by using primers represented by the sequences (SEQ ID NO:1), (SEQ ID NO:3) to (SEQ ID NO:10):

| 5'AAGTCATCTTTCGAGGTGAC3' | (SEQ ID NO:4) |
| 5'GAATTTTCTCTTCGGAGTTTA3' | (SEQ ID NO:5) |
| 5'GAGACATTCTTATATATG3' | (SEQ ID NO:3) |
| 5'GAAAATTCCTTTCGGGGA3' | (SEQ ID NO:1) |
| 5'CGACTAGGTGTTGGATGA3' | (SEQ ID NO:6) |
| 5'GAACGAAAGTTAAGGGAGT3' | (SEQ ID NO:7) |
| 5'ACTGAAGGAAGCAATCTAA3' | (SEQ ID NO:8) |
| 5'TCAGATACCGTCGTAATCTT3' | (SEQ ID NO:9) |
| 5'CCAAAGACTTTGATTTCTCAT3' | (SEQ ID NO:10) |

This invention allows all of the plasmodia, which infect the human, to be detected easily, rapidly and with a high sensitivity or distinguished accurately from one another, thus permitting treatment for malaria and large-scale mass examination in the area where malaria is prevalent.

7 Claims, 1 Drawing Sheet

Fig. 1

```
(a) AATCAA GAACGAAAGT CGGAGGTTC GAAGACGA TCAGATACCGTCGTAGT    1012
(b) AATCAA GAACGAAAGT TAAGGGAGT GAAGACGA TCAGATACCGTCGTAAT    1022
(c) AATCAA GAACGAAAGT TAAGGGAGT GAAGACGA TCAGATACCGTCGTAAT    1353
(d) AATCAA GAACGAAAGT TAAGGGAGT GAAGACGA TCAGATACCGTCGTAAT    1292
(e)                                       AGATACCGTCGTAAT
              ①                              ②

(a) TCC GACCATAAACGATGC CGAC------------ ---------------      1034
(b) CTT AACCATAAACTATGC CGACTAGGTGTTGGATGA AAGTGTTAAAAATA     1072
(c) CTT AACCATAAACTATGC CGACTAGGCTTTGGATGA AAGATTTTAAAATA     1403
(d) CTT AACCATAAACTATGC CGACTAGGTTTTGGATGA TAGTGTAAAAAATA     1342
(e) CTT AACCATAAACTATGC CGACTAGGTTTTGGATGA AACATTTTAAATA
                              ③

(a) --------CGGCGATGCG------GCGGCGTTATTCC CATGA--------      1062
(b) AAAGT----CATCT-TTCGAGGTGA-C--------TT- TT--AGATTGCTT     1108
(c) AGAAT----TTTCTCTTCGGAGTTT-A--------TTC TT--AGATTGCTT     1439
(d) AAAGAGACATTCTTATATATGAGTGT--------TTCTTT TTAGATAGCTT     1384
(e) AGAAAAT---TCCTTTCGGGGAAA---------TTTC
                                              ④

(a) CCCGCCGG GCAGCTT CCGGGAAACCAAAGTCTTTGG GTTCCGGGGGGAGT    1112
(b) CCTTCAGT AC--CTT ATGAGAAATCAAAGTCTTTGG GTTCTGGGGCGAGT    1154
(c) CCTTCAGT GC--CTT ATGAGAAATCAAAGTCTTTGG GTTCTGGGGCGAGT    1487
(d) CCTTCAGT AC--CTT ATGAGAAATCAAAGTCTTTGG GTTCTGGGGCGAGT    1432
(e)
                           ⑤
```

(a): Human being (Human. 963-1112)
(b): Falciparum malaria parasite (P.fal. 1022-1154)
(c): Tertian malaria parasite (P.viv. 1353-1487)
(d): Quartan malaria parasite (P.mal. 1292-1437)
(e): Ovale malaria parasite (P.oval)

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Synthetic DNA"

( i i i ) HYPOTHETICAL: NO ( i v ) ANTI-SENSE: NO ( v i ) ORIGINAL SOURCE:
( A ) ORGANISM: P. ovale ( x i ) SEQUENCE DESCRIPTION: SEQ ID NO:1:

GAAAATTCCT TTCGGGGA                                                                    18

( 2 ) INFORMATION FOR SEQ ID NO:2:

( i ) SEQUENCE CHARACTERISTICS:
        ( A ) LENGTH: 90 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: P.ovale ( x i ) SEQUENCE DESCRIPTION: SEQ ID NO:2:

AGATACCGTC GTAATCTTAA CCATAAACTA TGCCGACTAG GTTTGGATG AAACATTTTT          60

AAATAAGAAA ATTCCTTTCG GGGAAATTTC                                          90

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i i i ) HYPOTHETICAL: NO ( i v ) ANTI-SENSE: NO ( v i ) ORIGINAL SOURCE:
        ( A ) ORGANISM: P. malariae ( x i ) SEQUENCE DESCRIPTION: SEQ ID NO:3:

GAGACATTCT TATATATG                                                                    18

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i i i ) HYPOTHETICAL: NO ( i v ) ANTI-SENSE: NO ( v i ) ORIGINAL SOURCE:
        ( A ) ORGANISM: P. falciparum ( x i ) SEQUENCE DESCRIPTION: SEQ ID NO:4:

AAGTCATCTT TCGAGGTGAC                                                                  20

( 2 ) INFORMATION FOR SEQ ID NO:5:

( i ) SEQUENCE CHARACTERISTICS:
        ( A ) LENGTH: 21 base pairs
        ( B ) TYPE: nucleic acid (C) STRANDEDNESS: single
(D) TOPOLOGY: linear (i i) MOLECULE TYPE: other nucleic acid
(A) DESCRIPTION: /desc = "Synthetic DNA"

(i i i) HYPOTHETICAL: NO (i v) ANTI-SENSE: NO (v i) ORIGINAL SOURCE:
(A) ORGANISM: P. vivax (x i) SEQUENCE DESCRIPTION: SEQ ID NO:5:

GAATTTCTC TTCGGAGTTT A  21

(2) INFORMATION FOR SEQ ID NO:6:

(i) SEQUENCE CHARACTERISTICS:
(A) LENGTH: 18 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "Synthetic DNA"

(i i i) HYPOTHETICAL: NO (i v) ANTI-SENSE: NO (x i) SEQUENCE DESCRIPTION: SEQ ID NO:6:

CGACTAGGTG TTGGATGA  18

(2) INFORMATION FOR SEQ ID NO:7:

(i) SEQUENCE CHARACTERISTICS:
(A) LENGTH: 19 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "Synthetic DNA"

(i i i) HYPOTHETICAL: NO (i v) ANTI-SENSE: NO (x i) SEQUENCE DESCRIPTION: SEQ ID NO:7:

GAACGAAAGT TAAGGGAGT  19

(2) INFORMATION FOR SEQ ID NO:8:

(i) SEQUENCE CHARACTERISTICS:
(A) LENGTH: 19 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "Synthetic DNA"

(i i i) HYPOTHETICAL: NO (i v) ANTI-SENSE: YES (x i) SEQUENCE DESCRIPTION: SEQ ID NO:8:

ACTGAAGGAA GCAATCTAA  19

(2) INFORMATION FOR SEQ ID NO:9:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "Synthetic DNA"

( i i i ) HYPOTHETICAL: NO ( i v ) ANTI-SENSE: NO ( x i ) SEQUENCE DESCRIPTION: SEQ ID NO:9:

TCAGATACCG TCGTAATCTT                                                       20

( 2 ) INFORMATION FOR SEQ ID NO:10:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i i i ) HYPOTHETICAL: NO ( i v ) ANTI-SENSE: YES ( v i ) ORIGINAL SOURCE:
        ( A ) ORGANISM: P. falciparum ( x i ) SEQUENCE DESCRIPTION: SEQ ID NO:10:

CCAAAGACTT TGATTTCTCA T                                                  21

( 2 ) INFORMATION FOR SEQ ID NO:11:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc = "Synthetic DNA"

( x i ) SEQUENCE DESCRIPTION: SEQ ID NO:11:

TATTGAAAAT TCCTTTCGGG GA                                              22

( 2 ) INFORMATION FOR SEQ ID NO:12:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc = "Synthetic DNA"

( x i ) SEQUENCE DESCRIPTION: SEQ ID NO:12:

TATTGAGACA TTCTTATATA TG                                              22

( 2 ) INFORMATION FOR SEQ ID NO:13:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: other nucleic acid
     ( A ) DESCRIPTION: /desc = "Synthetic DNA"

( x i ) SEQUENCE DESCRIPTION: SEQ ID NO:13:

TTATCGACTA GGTGTTGGAT GA                                                                22

( 2 ) INFORMATION FOR SEQ ID NO:14:

( i ) SEQUENCE CHARACTERISTICS:
          ( A ) LENGTH: 150 base pairs
          ( B ) TYPE: nucleic acid
          ( C ) STRANDEDNESS: double
          ( D ) TOPOLOGY: linear ( i i ) MOLECULE TYPE: DNA (genomic)

( x i ) SEQUENCE DESCRIPTION: SEQ ID NO:14:

AATCAAGAAC GAAAGTCGGA GGTTCGAAGA CGATCAGATA CCGTCGTAGT TCCGACCATA        60

AACGATGCCG ACCGGCGATG CGGCGGCGTT ATTCCCATGA CCCGCCGGGC AGCTTCCGGG       120

AAACCAAAGT CTTTGGGTTC CGGGGGGAGT                                        150

( 2 ) INFORMATION FOR SEQ ID NO:15:

( i ) SEQUENCE CHARACTERISTICS:
          ( A ) LENGTH: 182 base pairs
          ( B ) TYPE: nucleic acid
          ( C ) STRANDEDNESS: double
          ( D ) TOPOLOGY: linear ( i i ) MOLECULE TYPE: DNA (genomic)

( x i ) SEQUENCE DESCRIPTION: SEQ ID NO:15:

AATCAAGAAC GAAAGTTAAG GGAGTGAAGA CGATCAGATA CCGTCGTAAT CTTAACCATA        60

AACTATGCCG ACTAGGTGTT GGATGAAAGT GTTAAAAATA AAAGTCATCT TTCGAGGTGA       120

CTTTTAGATT GCTTCCTTCA GTACCTTATG AGAAATCAAA GTCTTTGGGT TCTGGGGCGA       180

GT                                                                      182

( 2 ) INFORMATION FOR SEQ ID NO:16:

( i ) SEQUENCE CHARACTERISTICS:
          ( A ) LENGTH: 184 base pairs
          ( B ) TYPE: nucleic acid
          ( C ) STRANDEDNESS: double
          ( D ) TOPOLOGY: linear ( i i ) MOLECULE TYPE: DNA (genomic)

( x i ) SEQUENCE DESCRIPTION: SEQ ID NO:16:

AATCAAGAAC GAAAGTTAAG GGAGTGAAGA CGATCAGATA CCGTCGTAAT CTTAACCATA        60

AACTATGCCG ACTAGGCTTT GGATGAAAGA TTTTAAAATA AGAATTTTCT CTTCGGAGTT       120

TATTCTTAGA TTGCTTCCTT CAGTGCCTTA TGAGAAATCA AAGTCTTTGG GTTCTGGGGC       180

GAGT                                                                    184

( 2 ) INFORMATION FOR SEQ ID NO:17:

( i ) SEQUENCE CHARACTERISTICS:
          ( A ) LENGTH: 191 base pairs
          ( B ) TYPE: nucleic acid ( C ) STRANDEDNESS: double
( D ) TOPOLOGY: linear ( i i ) MOLECULE TYPE: DNA (genomic)

( x i ) SEQUENCE DESCRIPTION: SEQ ID NO:17:

| | | | | | |
|---|---|---|---|---|---|
| AATCAAGAAC | GAAAGTTAAG | GGAGTGAAGA | CGATCAGATA | CCGTCGTAAT | CTTAACCATA | 60
| AACTATGCCG | ACTAGGTTTT | GGATGATAGT | GTAAAAATA | AAAGAGACAT | TCTTATATAT | 120
| GAGTGTTTCT | TTTTAGATAG | CTTCCTTCAG | TACCTTATGA | GAAATCAAAG | TCTTTGGGTT | 180
| CTGGGGCGAG | T | | | | | 191

( 2 ) INFORMATION FOR SEQ ID NO:18:

( i ) SEQUENCE CHARACTERISTICS:
( A ) LENGTH: 90 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:18:

| | | | | | |
|---|---|---|---|---|---|
| AGATACCGTC | GTAATCTTAA | CCATAAACTA | TGCCGACTAG | GTTTTGGATG | AAACATTTTT | 60
| AAATAAGAAA | ATTCCTTTCG | GGGAAATTTC | | | | 90

DETECTION OF MALARIA

TECHNICAL FIELD

The present invention relates to a nucleotide fragment specific for an ovale malaria parasite (*Plasmodium ovale*) and/or a quartan malaria parasite (*Plasmodium malariae*) and a method of detecting a falciparum malaria parasite (*Plasmodium falciparum*), a tertian malaria parasite (*Plasmodium vivax*), a quartan malaria parasite and/or an ovale malaria parasite at the same time or in distinction from one another making good use of this nucleotide fragment.

BACKGROUND ART

Malaria is an infectious disease caused by the infection of a plasmodium and is carried by Anopheles mosquitoes. Malaria not only widely spreads all over the tropics, but also occurs in many of temperate regions. According to the report of World Health Organization (WHO), the putative numbers of cases and deaths amount to two hundred and seventy million and two million a year, respectively [World Health Organization: Malaria, "Tropical Disease in Research, 1989–1990" (8) UNDP/World Bank/WHO (TDR), WHO Geneva (1991), p. 29–40]. It is hence of urgent necessity to consider countermeasures. The countermeasures are centered on early detection and early treatment by mass examination. However, the present diagnosis does not cope with wide-range mass examination.

The microscopy in which a blood smear is Giemsa-stained and the stained sample is then observed through a microscope has heretofore been used in the diagnosis of malaria. The microscopy is cheap and can be simply practiced. On the other hand, its judgment requires much skill. Since the number of samples on which one inspection expert can test in a day is 60 to 70 specimens, such a method cannot cope with a great number of infected persons in the area where malaria is prevalent and the number of inspection experts is insufficient. In particular, when targets are subclinical persons as in mass examination, many of positive persons have a very few plasmodia in their blood. Therefore, it takes a long time to judge, and there is a great risk of making a wrong diagnosis as to the presence of a plasmodium and the kind of the plasmodium if present.

The serodiagnosis is widely practiced after the microscopy. The serodiagnosis is a method in which an antibody (which is said to lighten the symptoms upon infection though its activity is not so high that the infection is prevented) produced after infected with a plasmodium is detected, and techniques such as the indirect fluorescent antibody technique and ELISA (enzyme linked immunosorbent assay) have been developed. These methods permit the treatment of a large number of samples and are hence being widely used in mass examination and as means for immunological research studies even at present. However, such a method involves a problem in that even if the antibody is found to be positive by the serodiagnosis, this detection cannot distinguish infection at the time of the inspection from infection before then [Bruce-chwatt, L. J., Lancet 2,1509–1511 (1987)]. This method is clinically considered to be an ancillary diagnosis.

With the recent development of the molecular biology, it has also been conducted to detect plasmodia by DNA diagnosis. It has been reported that characteristic sequences consisting of many repetitions having a length of 20 to 30 bases exist in genes of plasmodia, probes specific for these regions as targets have been developed, which can achieve still higher sensitivity than that of probes making any other region as a target [Robert, H., Science 231, 1434–1436 (1986)]. However, this method has involved problems such as the detection requires hybridization, which makes use of a membrane and is hence complicated in operation, and the sensitivity is lower than expected when the method is clinically tested in practice [Lamar, D. E., Am. J. Trop. Med. Hyg. 34, 663–667 (1985)]. In order to enhance the sensitivity, a detection method making use of a gene-amplifying technique has thus been developed [Molec. Cell. Probes 4, 409–414 (1990)]. This method is a method in which a part of a 18S ribosome RNA gene of a falciparum malaria parasite is subjected to gene amplification to detect it.

However, since an area where falciparum malaria is prevalent often overlap an area where tertian malaria is prevalent, the detection of the falciparum malaria parasite alone according to the above-described method is insufficient to conduct effective treatment. Even if high-sensitive detection can be realized by the gene-amplifying reaction, the operation for the detection remains complicated. Accordingly, this method is far from the practical use as a means for mass examination under the circumstances.

In view of the foregoing circumstances, the present inventors found a nucleotide fragment specific for a falciparum malaria parasite, a nucleotide fragment specific for a tertian malaria parasite and a nucleotide fragment specific for both malaria parasites, and a method of detecting a falciparum malaria parasite and/or a tertian malaria parasite making good use of these nucleotide fragments, and previously filed an application for patent (Japanese Patent Application No. 36485/1992).

However, as plasmodia which infect the human, an ovale malaria parasite and a quartan malaria parasite are known in addition to the above-described plasmodia of two species. With respect to these four kinds of malaria, considerable skill is required to distinguish them from one another by morphological observation through a microscopy. In particular, the tertian malaria parasite and the ovale malaria parasite are extremely similar to each other in both morphology and clinical symptoms when infected with them and hence are very difficult to be distinguished from each other.

It is accordingly an object of the present invention to provide a nucleotide fragment specific for an ovale or quartan malaria parasite, by which only the ovale or quartan malaria parasite can be detected, and a method of detecting four species of plasmodia at the same time or in distinction from one another making good use of this nucleotide fragment.

DISCLOSURE OF THE INVENTION

According to the present invention, there is provided a nucleotide fragment comprising a base sequence (SEQ ID NO:1) represented by the following sequence (SEQ ID NO:1), a base sequence complementary thereto or a mutation sequence thereof; and a primer or probe for detecting an ovale malaria parasite comprising this nucleotide fragment.

5'GAAAATTCCTTTCGGGGA3'  (SEQ ID NO:1)

According to the present invention, there is also provided a nucleotide fragment comprising a base sequence (SEQ ID NO:2) represented by the following sequence (SEQ ID NO:2), a base sequence complementary thereto or a mutation sequence thereof; and a primer or probe for detecting an ovale malaria parasite comprising this nucleotide fragment.

5'AGATACCGTCGTAATCTTAACCATAAACTATGC
CGACTAGGTTTTGGATGAAACATTTTTAAATAA
GAAAATTCCTTTCGGGGAAATTTC3' (SEQ ID NO: 2)

According to the present invention, there is further provided a nucleotide fragment comprising a base sequence (SEQ ID NO:3) represented by the following sequence (SEQ ID NO:3), a base sequence complementary thereto or a mutation sequence thereof; and a primer or probe for detecting a quartan malaria parasite comprising this nucleotide fragment.

5'GAGACATTCTTATATATG3' (SEQ ID NO:3)

According to the present invention, there is still further provided a method of distinguishing falciparum malaria, tertian malaria, quartan malaria and ovale malaria from one another comprising using, as probes, nucleotide fragments separately comprising base sequences (SEQ ID NOS: 1, 3, 4, 5, and 6, respectively) respented by the following sequences (SEQ ID NOS:1, 3, 4, 5 and 6, base sequences complementary thereto or mutation sequences thereof.

| | |
|---|---|
| 5'AAGTCATCTTTCGAGGTGAC3' | (SEQ ID NO:4) |
| 5'GAATTTTCTCTTCGGAGTTTA3' | (SEQ ID NO:5) |
| 5'GAGACATTCTTATATATG3' | (SEQ ID NO:3) |
| 5'GAAAATTCCTTTCGGGGA3' | (SEQ ID NO:1) |
| 5'CGACTAGGTGTTGGATGA3' | (SEQ ID NO:6) |

According to the present invention, there is yet still further provided primers for detecting plasmodia comprising a nucleotide fragment comprising any one of base sequences (SEQ ID NOS:7-10, respectively) represented by the following sequences (SEQ ID NOS:7-10) or mutation sequences thereof.

| | |
|---|---|
| 5'GAACGAAAGTTAAGGGAGT3' | (SEQ ID NO:7) |
| 5'ACTGAAGGAAGCAATCTAA3' | (SEQ ID NO:8) |
| 5'TCAGATACCGTCGTAATCTT3' | (SEQ ID NO:9) |
| 5'CCAAAGACTTTGATTTCTCAT3' | (SEQ ID NO:10) |

When the nucleotide fragments according to the present invention, which have the above-mentioned base sequences, respectively, are used as a primer or primers either singly or in various combinations with one another, all of the plasmodia, which infect the human, namely, a falciparum malaria parasite, a tertian malaria parasite, a quartan malaria parasite and an ovale malaria parasite, can be detected easily, rapidly and with a high sensitivity at the same time or distinguished accurately from one another. Therefore, they are extremely advantageously used in treatment for malaria and large-scale mass examination in the area where malaria is prevalent.

BRIEF DESCRIPTION OF THE DRAWINGS

FIG. 1 illustrates the comparison of partial sequences of 18S ribosome RNA genes of a falciparum malaria parasite, a tertian malaria parasite, a quartan malaria parasite, an ovale malaria parasite and the human (SEQ ID NO:14-18). In the drawing, - means deletion. Numerals in parentheses indicate base sequence numbers. Underlines indicate regions respectively corresponding to primers or probes [(SEQ ID NOS:1, 3, 4 and 5 ] specific for the respective plasmodia. ①, ④, ② and ⑤ indicate regions respectively corresponding to primers represented by (SEQ ID NOS:1and 3–10). ③ indicates a region corresponding to a common probe represented by the sequence (SEQ ID NO:6).

BEST MODE FOR CARRYING OUT THE INVENTION

The nucleotide fragments represented by the sequences (SEQ ID NOS:1 and 3–10) in the present invention can be classified in the following manner according to their characteristics.

(A) A nucleotide fragment selectively detecting or amplifying only the 18S ribosome RNA gene of the ovale malaria parasite.

5'GAAAATTCCTTTCGGGGA3' (SEQ ID NO:1)

(B) A nucleotide fragment selectively detecting or amplifying only the 18S ribosome RNA gene of the quartan malaria parasite.

5'GAGACATTCTTATATATG3' (SEQ ID NO:3)

(C) A nucleotide fragment selectively detecting or amplifying only the 18S ribosome RNA gene of the falciparum malaria parasite.

5'AAGTCATCTTTCGAGGTGAC3' (SEQ ID NO:4)

(D) A nucleotide fragment selectively detecting or amplifying only the 18S ribosome RNA gene of the tertian malaria parasite.

5'GAATTTTCTCTTCGGAGTTTA3' (SEQ ID NO:5)

(E) Nucleotide fragments detecting or amplifying all of the 18S ribosome RNA genes of the falciparum malaria parasite, tertian malaria parasite, quartan malaria parasite and ovale malaria parasite.

| | |
|---|---|
| 5'CGACTAGGTGTTGGATGA3' | (SEQ ID NO:6) |
| 5'GAACGAAAGTTAAGGGAGT3' | (SEQ ID NO:7) |
| 5'ACTGAAGGAAGCAATCTAA3' | (SEQ ID NO:8) |
| 5'TCAGATACCGTCGTAATCTT3' | (SEQ ID NO:9) |
| 5'CCAAAGACTTTGATTTCTCAT3' | (SEQ ID NO:10) |

All of these nucleotide fragments can be chemically synthesized by means of a DNA synthesizer. The base sequence of the nucleotide fragment of (SEQ ID NO:1) was determined in the following manner. That is, blood was first collected from a patient infected with an ovale malaria parasite. DNA obtained from this was subjected to a gene-amplifying reaction using the primers of (SEQ ID NO:7–8). As a result, an amplified product of 140 bp was obtained. The base sequence of the amplified product was determined and found to be the following sequence (SEQ ID NO:2):

5'AGATACCGTCGTAATCTTAACCATAAACTATGC
CGACTAGGTTTTGGATGAAACATTTTTAAATAA
GAAAATTCCTTTCGGGGAAATTTC3' (SEQ ID NO: 2)

Of these nucleotide fragments, the nucleotide fragment having (SEQ ID NO:1) does not exist in the plasmodia of falciparum malaria, tertian malaria and quartan malaria and selectively detects or amplifies the 18S ribosome RNA gene of the ovale malaria parasite.

It was also confirmed that the nucleotide fragment of (SEQ ID NO:3) is synthesized by the DNA synthesizer and selectively detects or amplifies the 18S ribosome RNA gene of the quartan malaria parasite by a gene-amplifying reaction. In a similar manner, the reactivity of the nucleotide fragments of (SEQ ID NO:4-6) was also confirmed.

With respect to the mutation sequences in the nucleotide fragments according to the present invention, any mutation sequence may be mentioned so far as it functions as a primer or probe for detecting a falciparum malaria parasite, a tertian malaria parasite, a quartan malaria parasite and/or an ovale malaria parasite. Examples thereof include those in which part of bases are deleted from the original base sequences represented by (SEQ ID NOS:1-10) to, and those obtained by replacement or by addition of other bases. More specifically, there may be mentioned base sequences corresponding to their corresponding regions of genes of the mutated strains of the above-described plasmodia, RNA sequences corresponding to these genes and the like. However, it is preferred that there be no mutations, if any, little in the vicinity of the 3'-terminals of the primers which seem to greatly affect efficacies of the elongation reaction of the primers. It is more preferred that there be mutations in the vicinity of the 5'-terminals of the primers.

In order to detect the four species of plasmodia using the nucleotide fragments according to the present invention as primers or probes, it is preferred that these nucleotide fragments be used in the form of labeled fragments or solid carrier binding site-introduced fragments.

The labeled products of the nucleotide fragments according to the present invention include those obtained by binding a detectable label to the above-described nucleotide fragments. In the present invention, either non-radioactive substances or radioactive substances may be available as the label, with the non-radioactive substances being preferred. Examples of the non-radioactive substances include fluorescent substances [for example, fluorescein and its derivatives (fluorescein isothiocyanate and the like), rhodamine and its derivatives (tetramethylrhodamine isothiocyanate, texasred and the like)], chemiluminescent substances (for example, acridine and the like), delayed fluorescence-emitting substances (DTTA: product of Pharmacia Co.), which can be directly detected.

When substances specifically binding to the above-mentiabove-mentioned labels are utilized for detecting these labels, the labels can be indirectly detected. Biotin or some haptens are mentioned as labels in such a case. In the case where biotin is used, avidin or streptavidin which specifically couples to biotin can be used. In the case where the haptens are used, antibodies which specifically couple to the haptens can be used. Compounds having a 2,4-dinitrophenyl group and digoxigenin, and besides biotin and fluorescent substances can be used as haptens. These labels may be introduced into the primers either singly or, if necessary, in various combinations with one another in accordance with the conventionally-known methods (see Japanese Patent Application Laid-Open Nos. 93098/1984 and 93099/1984).

The solid carrier binding site-introduced derivatives of the nucleotide fragments according to the present invention include those obtained by introducing sites capable of coupling to a solid carrier into the nucleotide fragments according to the present invention. For example, the above-mentioned non-radioactive labels may also be used as the sites capable of coupling to the solid carrier (solid carrier binding sites). Preferable examples thereof include biotin, fluorescent substances such as fluorescein, and haptens such as compounds having a 2,4-dinitrophenyl group and digoxigenin. These sites may be introduced into the nucleotide fragments according to the present invention in advance either singly or, if necessary, in various combination with one another. In order to selectively bind the site to the solid carrier, the substance for the site may preferably be different from that for the label. The solid carrier in the present invention should be inactive against solvents and all reagents to be used in reactions, can be separated from solutions of the reagents by any known method and is able to selectively couple to the above-described sites. Examples of such a solid carrier include solid materials such as microtiter plates, polystyrene balls, agarose beads and polyacryl beads, in which streptavidin, an antibody or the like capable of trapping the above sites has been introduced. The microtiter plates are preferred because they are excellent in operating characteristics, mechanization and the like.

For example, a carrier in which streptavidin has been introduced can be used in order to trap a product formed by a gene-amplifying reaction making use of a primer in which biotin has been introduced. Besides, in order to trap a product formed by a gene-amplifying reaction making use of a primer in which a fluorescein residue or a 2,4-dinitrophenyl group has been introduced, a carrier in which its corresponding antibody has been introduced can be used.

In order to detect the plasmodia with these probes, a dot blot hybridization technique, a Southern hybridization technique or the like may be used [Hames, B. D., Nucleic Acid Hybridization, IRL Press (1985)]. As a target for the detection, not only DNA but also RNA may be used. In the present invention, 18S ribosome RNA, which is large in copy number per cell, can be used as a target to enhance sensitivity. When the detection must be conducted with still higher sensitivity, various gene-amplifying reactions can be used. When products formed by these reactions are used as targets, the sensitivity can be enhanced by leaps and bounds. For example, there may be conducted dot blot hybridization or reverse dot hybridization in which PCR is adopted as the gene-amplifying reaction, and a product formed by the PCR is used as a target [Innis, M. A., PCR. Protocols Academic Press (1990)]. Further, when high-sensitive and easy detection is required, a method making use of a microtiter plate as described in Japanese Patent Application Laid-Open No. 182035/1991 is more practical.

The detection of the four species of plasmodia by the gene-amplifying reactions making use of the nucleotide fragments according to the present invention is basically performed in the following manner.

In the case where the four species of plasmodia may not be distinguished from one another, that is, one wants to determine whether he is infected with a plasmodium or not, it is only necessary to conduct a gene-amplifying reaction with a primer selected from the sequences (SEQ ID NOS:7) or a primer selected from the base sequence represented by (SEQ ID NO:2) and then to determine the presence of a product of the intended size formed by the gene-amplifying reaction by agarose gel electrophoresis or the like. More simply, as described in Japanese Patent Application Laid-Open No. 252300/1989, one primer in which a label has been introduced, and the other primer in which a solid carrier binding site has been introduced may be used to conduct a gene-amplifying reaction, and the resulting amplified product may be detected by a reaction like ELISA (enzyme linked immunosorbent assay).

On the other hand, in the case where the four species of plasmodia must be distinguished from one another, it is possible to make a good use of the fact that the chain lengths of products formed by gene-amplifying reactions with primers of (SEQ ID NOS:1, and 3-6) or primers selected from the base sequence represented by (SEQ ID NOS:1, and 3-6) delicately vary according to the species of malaria, or that when a product formed by a gene-amplifying reaction is subjected to a treatment with a restricted enzyme, a fragment inherent in each of the malaria species is formed. A simpler method is a method in which gene-amplifying reactions are conducted with primers represented by (SEQ ID NO:7-10) or primers selected from the base sequence represented by (SEQ ID NO:2), and the resulting amplified products are used as targets to conduct detection with probes represented by (SEQ ID NOS:1, and 3-6) or probes selected from the base sequence represented by (SEQ ID NO:2). For example, there is a method in which a gene-amplifying reaction is conducted with a primer selected from (SEQ ID NOS:6–10) or a primer selected from the base sequence represented by the sequence (SEQ ID NO:6–1), in which a label has been introduced, and a product formed by this gene-amplifying reaction is hybridized with each of probes of (SEQ ID NO:1, and 3–6), which have been immobilized to wells of microtiter plates, thereby making detection.

The operation of the detection method according to the present invention will hereinafter be described in detail.

(1) Pretreatment of specimen

There are first provided specimens to be detected for the presence of the target plasmodium. Examples of the specimens principally include blood obtained from infected persons or patients. The hemocytes of the blood collected can be lysed with a surfactant or the like [for example, saponin, Biochem. Biophys. Res. Commun., 175, 179–184 (1991)] after its serum component is removed or as it is, thereby removing the hemocytes by centrifugation. With respect to the plasmodium from which the hemocytes have been removed, its cells can be lysed by a treatment with a proteinase like the ordinary cells.

For the sake of simplified operation, it is necessary to omit the centrifugation. In this case, care must be taken because a DNA polymerase reaction tends to be extremely inhibited by the blood components. For example, the whole blood may be treated with the above-mentioned saponin and then treated with a proteinase or the like as it is, thereby providing a sample for gene amplification. In this case, however, it is preferred that the pH of the blood after the cell-lysing reaction be measured in advance to add buffer as described above upon the cell-lysing treatment or gene-amplifying reaction so as to give a pH most suitable for the DNA polymerase reaction. When the whole blood is subjected to the lysing treatment, its pH is lowered. Therefore, it is preferred that the pH and concentration of the buffer to be used be kept higher than those generally used in cell lysis and gene-amplifying reaction in order to optimize the pH in the DNA polymerase reaction.

(2) Gene-amplifying reaction

If the target plasmodium is present in the specimen, a gene-amplifying reaction according to the elongation reaction of primers may be carried out by adding the primers according to the present invention to the specimen.

The elongation reaction of a primer can be carried out by introducing four kinds of nucleoside triphosphates [deoxyadenosine triphosphate, deoxyguanosine triphosphate, deoxycytidine triphosphate and thymidine triphosphate (a mixture thereof may be referred to as dNTP)] as substrates into the primer.

In the elongation reaction, E. coli DNA polymerase I, Klenow fragment from E. coli DNA polymerase I, T4 DNA polymerase and the like are used. In particular, when a heat-resistant enzyme such as a Taq polymerase, which causes the elongation reaction at a high temperature, is used, specificity of primer's recognition of a target sequence can be enhanced (refer to Japanese Patent Application Laid-Open Nos. 314965/1989 and 252300/1989 for further particulars).

The 18S ribosome RNA gene of the target plasmodium can be effectively amplified by repeating the elongation reaction using a combination [for example, a combination of the primer (SEQ ID NO:7) with the primer (SEQ ID NO:8), a combination of the primer (SEQ ID NO:9) with the primer (SEQ ID NO:10), a combination of the primer (SEQ ID NO:7) with the primer (SEQ ID NO:10) or a combination of the primer (SEQ NO:9) with the primer (SEQ ID NO:8)] of two kinds of the primers according to the present invention.

Further detailed procedures of the gene-amplifying reaction should be referred to reference books ["Jikken Igaku (Experimental Medicine), 8, No. 9 (1990), Yodosha, and "PCR Technology", Stockton Press (1989)].

(3) Detection

Detection of a conjugate of the target gene with a detection primer produced by a primer elongation reaction leads to detection of the plasmodium in the specimen. A preferred detection method varies according to the kind or form of the above-mentioned primer elongation product, i.e., a synthesized nucleic acid.

In general, the product formed by the gene-amplifying reaction forms a double stranded DNA. Therefore, this synthesized nucleic acid can be detected by electrophoresis [Saiki, R. K., Science, 230, 1350–1354 (1985)], dot hybridization making use of labeled probes [Saiki, R. K., Nature, 324, 163–166 (1986)] or the like.

When a label has been introduced into a synthesized nucleotide chain, the nucleic acid can also be detected by reverse dot hybridization [Saiki, R. K., Proc. Natl. Acad. Sci. U.S.A., 86, 6230–6234 (1989)], in which the labeled and synthesized nucleotide chain is hybridized with a probe immobilized on a solid carrier, a column method making use of a solid adsorbent (see Japanese Patent Application Laid-Open No. 314965/1989) or the like.

The nucleic acid can be detected with greater ease according to the method described in Japanese Patent Application Laid-Open No. 252300/1989. That is, there is a method in which a combination of the solid carrier binding site-introduced derivative of the nucleotide fragment with the labeled fragment is used as a primer, a product formed by the gene-amplifying reaction is brought into contact with a solid carrier, and impurities are then removed by washing with an appropriate solvent. Even in this method, the chain of the synthesized nucleic acid elongated by the primer having the solid carrier binding site forms a double stranded DNA with another synthesized nucleic acid elongated by the labeled primer. Therefore, the target product formed by the gene-amplifying reaction is immobilized on the solid carrier in the form bearing the label thereon, resulting in specific fixation.

When a plasmodium is detected in distinction from other plasmodia, it is very simple and practical to use the method described in Japanese Patent Application Laid-Open No. 227998/1993. That is, there is a method in which the non-radioactive label-introduced fragment is used as a primer to conduct a gene-amplifying reaction, and the resulting reaction product is hybridized with the nucleotide fragments of (SEQ ID NO:6–10) immobilized to wells of microtiter plates. Only when a sequence complementary to a nucleotide fragment immobilized to the wells of a microtiter plate exists, the product formed by the gene-amplifying reaction is bound to the microtiter plate. In this case, it is only necessary to detect the label bound to the primer.

The detection of the label may be performed by any conventional method according to the label used. For example, in the case where the label is a radioisotope, it is only necessary to measure the radioactivity thereof as it is. In the case where the label is biotin or a hapten, the substrate may be reacted with an avidin ( or streptavidin)-enzyme conjugate or an antibody-enzyme conjugate, respectively, thereby obtaining a component detectable by a staining or fluorescent means. Besides, for example, in the case where the label is a fluorescent substance, it is only necessary to measure the fluorescent intensity by means of a fluorometer as it is.

EXAMPLES

The present invention will hereinafter be described in detail with reference to the following examples. However, this invention is not intended to be limited to these examples only.

9

Example 1

Synthesis of deoxyoligonucleotide and primer:

First of all, an oligonucleotide was synthesized on the basis of the phosphoamidite method of Caruthers et al. [Tetrahedron Lett., 22, 1859 (1981)] by means of a DNA synthesizer Model 318A manufactured by Applied Biosystems Co. on the scale of 0.2 micromole.

On the other hand, an oligonucleotide in which a label or a solid carrier binding site was introduced was obtained by synthesizing an oligonucleotide in the 5'-terminal of which an aminoalkyl group was introduced and then introducing the label or the solid carrier binding site in the oligonucleotide with an appropriate reagent. Examples of these syntheses are described below.

First, an oligonucleotide (5'GAACGAAAGTTAAGGGAGT; SEQ ID NO: 7) in the 5'-terminal of which an aminoalkyl group was introduced was synthesized by means of the DNA synthesizer Model 318A manufactured by Applied Biosystems Co. A protective mononucleotide phosphoamidite was successively added to 0.2 micromole of a support to add a base to the 5'-terminal, and Aminolink II (trade name, Applied Biosystems Co.) was then added further. The addition product thus obtained was then separated from the support by a treatment with concentrated aqueous ammonia, and the protecting group was removed.

After the deblocking, the thus-obtained product was subjected to gel filtration through Sephadex G-50. Fractions of the peak eluted first were collected and concentrated. A 1M aqueous solution of NaHCO$_3$ (10 µl), H$_2$O (30 µl) and a solution of biotin N-hydroxysuccinimide ester (BRL Co., Ltd) in DMF (20 µg/µl, 50 µl) were then added to the thus-obtained aqueous solution of the aminoalkylated oligonucleotide (1 O.D.: 10 µl). After mixing them, the mixture was allowed to stand at room temperature. After 4 hours, the mixture was passed through a gel filtration column (Sephadex G-50), and elution was effected with 50 mM TEAB buffer (a buffer solution of triethylammonium bicarbonate, pH 7.5). Fractions of the peak eluted first were collected to dry into solid. This sample was then purified by reverse-phase HPLC (column: µ-Bondapak C18, eluent: 5–20% acetonitrile-50 mM triethylammonium acetate, pH 7.0, yield: 0.35 O.D.).

An oligonucleotide (5'ACTGAAGGAAGCAATCTAA; SEQ ID NO:8) in the 5'-terminal of which a dinitrophenyl group (DNP) was introduced was obtained by first synthesizing an oligonucleotide in which an aminoalkyl group was introduced as in the case of the biotinylated oligonucleotide and using this as a starting material. To a solution of the aminoalkylated oligonucleotide (1.0 O.D., 180 µl) roughly purified by gel filtration, was added 1M NaHCO$_3$ (20 µl), to which a 5% (v/v) ethanol solution of dinitrofluorobenzene (100 µl) was then added. The resultant mixture was heated at 37° C. for 2 hours. After completion of the reaction, the reaction mixture was subjected to gel filtration in the same manner as in the biotinylated oligonucleotide to remove reagents, and purified by reverse-phase HPLC (yield: 0.38 O.D.).

Example 2

Determination of base sequence of 18S ribosome RNA gene of *Plasmodium ovale* (ovale malaria parasite):

Genes of an ovale malaria parasite were extracted from the blood of a patient who had been judged to be infected with the ovale malaria parasite from the observation of a blood smear. The blood (5 ml) containing the ovale malaria parasite was first suspended in PBS, and the suspension was centrifuged for 10 minutes at 3,000 rpm. The supernatant was removed, and the resultant hemocytes were suspended in a 0.15% (w/v) PBS solution of saponin (7.5 ml), and the suspension was left at rest for 20 minutes at 37° C. PBS was then added to 45 ml, and the dilute suspension was centrifuged for 15 minutes at 3,000 rpm. The sediment was suspended in PBS (45 ml), and the suspension was centrifuged similarly. This process was further repeated twice. The thus-obtained sediment was suspended in PBS (50 µl) and transferred to a 2-ml centrifuge tube. This suspension was centrifuged for 5 minutes at 10,000 rpm. The supernatant was removed, and the sediment was suspended in a mixture (1.5 ml) of 10 mM Tris-HCl (pH 7.5), 1 mM EDTA (pH 8.0) and 0.1M NaCl. Further, 20% SDS (37.5 µl) and proteinase K (10 µg/µl, 30 µl) were added to the suspension, followed by end-over-end mixing at room temperature for 1 hour. The resulting mixture was left at stand for 16 hours at 37° C. Saturated saline was added to this mixture in an amount third of the volume of the mixture, followed by end-over-end mixing. The resulting mixture was left at rest for 15 minutes at room temperature and then centrifuged for 15 minutes at 15,000 rpm. Hereinafter, the resultant supernatant was treated in accordance with the conventional procedures (treatment with phenol, washing with chloroform, precipitation with ethanol) for DNA extraction. The DNA sediment finally obtained was dried and dissolved in water (240 µl) to prepare a solution of ovale malaria DNA.

A part of the 18S ribosome RNA gene of the ovale malaria parasite was subjected to gene amplification. That is, 35 µl of a lysis solution [100 mM Tris-HCl (pH 8.9), 1.5 mM MgCl$_2$, 80 mM KCl, 500 µg/ml of BSA, 0.1% (w/v) sodium cholate, 0.1% Triton X-100, 200 µg/ml of proteinase K, 0.45% Tween 20 and 0.45% NP40], and one drop of mineral oil were added, and the mixture was heated for 10 minutes at 95° C. To this mixture, were added 10 µl of a liquid PCR mixture [biotin-labeled primer (SEQ ID NO:7) (Bio-5'GAACGAAAGTTAAGGGAGT, 5 µg/ml), primer (SEQ ID NO:8) (5'ACTGAAGGAAGCAATCTAA, 5 µg/ml), dATP, dGTP, dCTP and TTP (each 1 mM), 50 mM Tris-HCl (pH 8.9), 80 mM KCl 1.5 mM MgCl$_2$, 0.1% Triton X-100, 0.1% (w/v) sodium cholate, 500 µg/ml of BSA, and 1 U Tth DNA polymerase] and the above-prepared ovale malaria parasite DNA solution (5 µl) to perform a gene-amplifying reaction by means of a thermal cycler (PJ2000, manufactured by Perkin Elmer Co.) under conditions of 94° C. for 30 seconds, 50° C. for 60 seconds, and 72° C. for 60 seconds (15 cycles). The liquid reaction mixture (1 µl) was taken out and added to a lysis solution (39 µl) subjected to a heat treatment at 94° C. for 10 minutes, thereby performing a gene-amplifying reaction (25 cycles) under the same conditions as described above. A part of the liquid reaction mixture was taken out and determined by agarose gel electrophoresis. As a result, a product of about 140 bp was able to be identified.

Streptavidin-immobilizing beads (Dynabeads, M280 Streptavidin, product of Dynal Co., 20 µl) were then washed with a cleaning solution (10 mM Tris-HCl, pH 7.5; 1 mM EDTA; 2M NaCl, 20 µl). These beads were suspended in the cleaning solution (40 µl), and the above-prepared ovale malaria parasite DNA solution (5 µl) was added to the resultant suspension. The resultant mixture was mixed and left at rest for 15 minutes at room temperature. The supernatant was removed, and the residue was washed with the cleaning solution (40 µl). Then, 0.1M NaOH (10 µl) was added, and the resultant mixture was left at rest for 10 minutes at room temperature. The supernatant was taken out and neutralized with 0.33M HCl (3 µl) to provide Solution B. The residual beads were washed with 0.1M NaOH (50 µl), the cleaning solution (40 µl), and 10 mM Tris-HCl (pH 7.6) and 0.1 mM EDTA (pH 8.0, 50 µl), and suspended in water (8 µl) to provide Suspension A.

The primer (SEQ ID NO:8) (5'4ACTGAAGGAAGCAATCTAA) and the primer (SEQ

ID NO:7) (Bio-5'GAACGAAAGTTAAGGGAGT) were used for Solution A and Suspension B, respectively, to determine base sequences in accordance with the dideoxy method.

Example 3

Preparation of probe immobilized to wells of microtiter plate:

Oligonucleotides represented by the following sequences (A) (ovale malaria parasite), (B) (quartan malaria parasite) and (C) (common to falciparum, tertian, quartan and ovale malaria parasites) were synthesized, and their 5'-terminals were phosphorylated with a T4 polynucleotide phosphorylase and ATP. Their corresponding two oligonucleotides were mixed to form double stranded fragments (SEQ ID NO:11–13).

(A) 5' pTATTGAAAATTCCTTTCGGGGA 3' (SEQ ID NO: 10)
3' CTTTTAAGGAAAGCCCCTATAAp 5' (SEQ ID NO: 11)

(B) 5' pTATTGAGACATTCTTATATATG 3' (SEQ ID NO: 12)
3' CTCTGTAAGAATATATACATAAp 5' (SEQ ID NO: 13)

(C) 5' pTTATCGACTAGGTGTTGGATGA 3' (SEQ ID NO: 14)
3' GCTGATCCACAACCTACTAATAp 5' (SEQID NO: 15)

These fragments were separately bound to each other with a T4 DNA ligase, and the resultant conjugates were treated with a Klenow fragment from *E. coli* DNA polymerase I and four kinds of deoxyribonucleoside triphosphates to make them blunt ends. A plasmid, pUC-Sfix2 (Japanese Patent Application Laid-Open No. 190194/1990) was excised with a restriction enzyme, BamH I, and the resultant fragments were then made blunt ends with the Klenow fragment. These DNA fragments were bound using the T4 DNA ligase to transform *E. coli* DH5. The intended clones were selected by the restriction enzyme analysis. The thus-obtained plasmid was excised with a restriction enzyme Sfi I, and fragments containing repetition of each of the above sequences were purified and recovered by using electrophoresis. A fragment excised with Sfi I and containing excessive repetition of the sequence were bound to a vector with the T4 DNA ligase. In this case, a fragment obtained by excising pUC-Sfix2 with Sfi I was used as the vector. This conjugate was used to transform MV1184, and clones each containing about 60 units of (SEQ ID NOS:10–15) were separately selected by restriction enzyme analysis.

From these clones, single stranded DNAs were prepared with a helper phage M13KO7 in accordance with the conventional method [Molecular cloning, 4.29–4.32, 2nd ed.].

Each of the single stranded DNAs thus obtained was diluted to a concentration of 1 µg/50 µl with a solution containing 10 mM Tris-HCl (pH 7.6) and 1 mM EDTA, and an equiamount of a buffer for immobilization [1.5M NaCl, 0.3M Tris-HCl (pH 8.0), 0.3M MgCl$_2$] was added to the dilute solution. The mixture was mixed and added to wells of a microtiter plate (Sepaplate 8F H type, Sumitomo Bakelite Co., Ltd.) in an amount of 100 µl per well. The wells were covered and left at rest for 16 hours at 37° C. Thereafter, the solution was removed from the wells, and the microtiter plate was dried at 37° C. for 30 minutes. UV Stratalinker™2400 (product of Stratagene Co.) was then used to carry out irradiation of 500,000 µJ. After the irradiation, the microtiter plate was washed 3 times with a cleaning buffer [1M NaCl, 2 mM MgCl$_2$, 0.1M Tris-HCl (pH 9.3), 0.1% Tween 20; 200 µl]. The microtiter plate on which the single stranded DNA containing (SEQ ID NOS:10–11) was immobilized, the microtiter plate on which the single stranded DNA containing (SEQ ID NOS:12–13) was immobilized, and the microtiter plate on which the single stranded DNA containing (SEQ ID NOS:14–15) was immobilized were provided as microtiter plates for detecting the ovale malaria parasite, the quartan malaria parasite and all of the four plasmodia, respectively. The microtiter plates were conserved at 4° C.

Example 4

Simultaneous detection of falciparum malaria parasite, tertian malaria parasite and ovale malaria parasite:

DNAs extracted from plasmodia were used as samples [A: falciparum malaria parasite (0.22 ng/µl, 5 µl), B: tertian malaria parasite (DNA corresponding to 10$^4$ parasites isolated from a patient), C: ovale malaria parasite (DNA solution obtained in Example 2, 5 µl), D: DNA obtained from leukocytes of the healthy human (100 ng/µl, 5 µl)]. Solutions of the DNAs were separately added to 40 82 l of a lysis solution [100 mM Tris-HCl (pH 8.9), 1.5 mM MgCl$_2$, 80 mM KCl, 500 µg/ml of BSA, 0.1% (w/v) sodium cholate, 0.1% Triton X-100, 200 µg/ml of proteinase K, 0.45% Tween 20 and 0.45% NP40]. After the mixtures were treated at 60° C. for 20 minutes and at 94° C. for 10 minutes, 10 µl of a liquid PCR mixture [biotin-labeled primer (SEQ ID NO:7) and DNP-labeled primer (SEQ ID NO:8) (each 5 µg/ml), dATP, dGTP, dCTP and TTP (each 1 mM), 50 mM Tris-HCl (pH 8.9), 80 mM KCl, 1.5 mM MgCl$_2$, 0.1% Triton X-100, 0.1% (w/v) sodium cholate, 500 µg/ml of BSA, and 1 U Tth DNA polymerase] were added to the samples to carry out respective gene-amplifying reactions (under conditions of 94° C. for 30 seconds, 50° C. for 60 seconds and 72° C. for 60 seconds, and 30 cycles).

After completion of the reactions, each 10 µl of the liquid reaction mixtures were added to streptavidin-immobilized wells of a microtiter plate, to which an alkaline phosphatase-labeled anti-DNP antibody diluted with 100 µl of a buffer [50 mM Tris-HCl (pH 7.5), 0.15 mM MgCl$_2$, 0.05% Tween 20] had been added in advance. After left over for 30 minutes at room temperature, the wells were washed with about 300 µl of the above-described buffer. This washing process was repeated further twice, and 100 µl of a solution of p-nitrophenylphosphate (dissolved in 4 mg/ml of mg/ml of a diethanolamine buffer) was added to the wells. After left over for 30 minutes at 25° C., the absorbance at 405 nm as to the respective wells was measured by a microplate reader. As a result, all of the plasmodia were able to be detected by using the primers according to the present invention as shown in Table 1.

TABLE 1

| Simultaneous detection of falciparum, tertian and ovale malaria parasites | | | |
|---|---|---|---|
| Falciparum malaria parasite (A) | Tertian malaria parasite (B) | Ovale malaria parasite (C) | Healthy human (D) |
| Found 0.67 | 0.97 | 0.44 | 0.08 |

Example 5

Simultaneous and distinctive detection of falciparum malaria parasite, tertian malaria parasite and ovale malaria parasite:

After the same samples A, B, C and D as those used in Example 4 were treated with the lysis solution in the same manner as in Example 4, 10 µl of a liquid PCR mixture [biotin-labeled primer (SEQ ID NO:9) (Bio-5'TCAGATACCGTCGTAATCTT) and biotin-labeled primer (SEQ ID NO:10) (Bio-5'CCAAACACTTTGATTTCTCAT) (each 5 µg/ml), dATP, dGTP, dCTP and TTP (each 1 mM), 50 mM Tris-HCl (pH 8.9), 80 mM KCl, 1.5 mM $MgCl_2$, 0.1% Triton X-100, 0.1% (w/v) sodium cholate, 500 µg/ml of BSA, and 1 U Tth polymerase] were added to the samples to carry out respective gene-amplifying reactions (under conditions of 94° C. for 30 seconds, 50° C. for 60 seconds and 72° C. for 60 seconds, and 30 cycles). After completion of the reactions, each of the liquid reaction mixtures was subjected to thermal denaturation for 5 minutes on a boiling water bath, and then quenched on an ice bath. Each 10 µl of the liquid mixture were added to wells of the microtiter plates for detecting the falciparum malaria parasite, the tertian malaria parasite, the ovale malaria parasite, the quartan malaria parasite and all of the four plasmodia, respectively, to which a solution for hybridization (5×SSC: 10 µl/well) had been added in advance, thereby performing hybridization at 60° C. for 1 hour. The hybridization solution was removed from the wells, and the wells were washed 3 times with 2×SSC (200 µl/well). To the wells thus washed, was added a streptavidin-alkaline phosphatase solution [diluting streptavidin-alkaline phosphatase produced by BRL Co. to 1/2000 with 0.1M Tris-HCl (pH 7.5), 0.3M NaCl and 2 mM $MgCl_2$, 0.05% (v/v) Triton X-100; 100 µl/well]. The thus-treated microtiter plates were left over for 15 minutes at room temperature. The liquid reaction mixtures were removed from the respective wells, and the wells were washed 3 times with a cleaning solution [0.1M Tris-HCl (pH 7.5), 0.3M NaCl, 2 mM $MgCl_2$, 0.05% (v/v) Triton X-100; 200 µl/well). After the washing, a solution of p-nitrophenylphosphate (in 1M diethanolamine (pH 9.8) and 0.5 mM $MgCl_2$; 4 mg/ml; 100 µl/well) was added to the wells to conduct reaction at 25° C. for 30 minutes, and the absorbance at 405 nm as to the respective wells was measured. As a result, all of the four plasmodia were able to be simultaneously detected in distinction from one another by using the primers according to the present invention as shown in Table 2.

TABLE 2

Simultaneous and distinctive detection of falciparum, tertian and ovale malaria parasites

| | | Sample | | | |
|---|---|---|---|---|---|
| | Well | Falciparum malaria parasite (A) | Tertian malaria parasite (B) | Ovale malaria parasite (C) | Healthy human (D) |
| Found | Well for detection of falciparum malaria parasite | 1.43 | 0.00 | 0.00 | 0.03 |
| | Well for detection of tertian malaria parasite | 0.01 | 1.82 | 0.00 | 0.02 |
| | Well for detection of ovale malaria parasite | 0.00 | 0.00 | 0.66 | 0.00 |
| | Well for detection of quartan malaria parasite | 0.00 | 0.00 | 0.00 | 0.00 |

According to the present invention, all of the plasmodia (falciparum, tertian, quartan and ovale malaria parasites), which infect the human, can be detected easily, rapidly and with a high sensitivity or distinguished accurately from one another. Therefore, the invention is useful in treatment for malaria and large-scale mass examination in the area where malaria is prevalent.

We claim:

1. A nucleotide fragment consisting of a base sequence represented by the following sequence:

5'GAAAATTCCTTTCGGGGA3'  (SEQ ID NO:1)

or the base sequence complementary thereto.

2. A nucleotide fragment consisting of a base sequence represented by the following sequence:

5'AGATACCGTCGTAATCTTAACCATAAACTATGC
CGACTAGGTTTTGGATGAAACATTTTTAAATAA
GAAAATTCCTTTCGGGGAAATTTC3'  (SEQ ID NO: 2)

or the base sequence complementary thereto.

3. A nucleotide fragment consisting of a base sequence represented by the following sequence:

5'GAGACATTCTTATATATG3'  (SEQ ID NO:3)

or the base sequence complementary thereto.

4. A method of distinguishing falciparum malaria, tertian malaria, quartan malaria and ovale malaria from one another comprising hybridizing a nucleotide fragment consisting of a base sequence represented by one of the following sequences:

| | |
|---|---|
| 5'AAGTCATCTTTCGAGGTGAC3' | (SEQ ID NO:4) |
| 5'GAATTTTCTCTTCGGAGTTTA3' | (SEQ ID NO:5) |
| 5'GAGACATTCTTATATATG3' | (SEQ ID NO:3) |
| 5'GAAAATTCCTTTCGGGGA3' | (SEQ ID NO:1) |
| 5'CGACTAGGTGTTGGATGA3' | (SEQ ID NO:6) | or the base sequences complementary thereto to a sample DNA in which falciparum malaria, tertian malaria, quartan malaria or ovale malaria is to be detected, detecting binding of said nuclecide fragment to said sample DNA, and correlating binding of said nucleotide fragment to said sample DNA to the presence of one of falciparum malaria, tertian malaria, quartan malaria or ovale malaria.

5. Primers for detecting plasmodia each consisting of a nucleotide fragment consisting of the one of the base sequences represented by the following sequences:

| | |
|---|---|
| 5'GAACGAAAGTTAAGGGAGT3' | (SEQ ID NO:7) |
| 5'ACTGAAGGAAGCAATCTAA3' | (SEQ ID NO:8) |
| 5'TCAGTTACCGTCGTAATCTT3' | (SEQ ID NO:9) | and

| | |
|---|---|
| 5'CCAAAGACTTTGATTTCTCAT | (SEQ ID NO:10). |

6. A primer or probe for detecting an ovale malaria parasite consisting of a nucleotide fragment comprising a base sequence represented by the following sequence:

5'GAAAATTCCTTTCGGGGA3'  (SEQ ID NO:1), the base sequence complementary thereto or a mutation sequence thereof, wherein said primer or probe specifically detects an ovale malaria parasite under the following conditions:

(A) amplification in 100 mM Tris-HCl (pH 8.9), 1.5 mM MgCl$_2$, 80 mM KCl, 500 µg/ml BSA, 0.1% (w/v) sodium cholate, 0.1% Triton X-100, 200 µg/ml of proteinase K, 0.45% Tween 20 and 0.45% NP40 under conditions of 94° C. for 30 seconds, 50° C. for 60 seconds, and 72° C. for 60 seconds; or (B) hybridization in 5×SSC at 60° C. for 1 hour.

7. A primer or probe for detecting an ovale malaria parasite consisting of a nucleotide fragment comprising a base sequence represented by the following sequence:

```
5'AGATACCGTCGTAATCTTAACCATAAACTATGC
CGACTAGGTTTTGGATGAAACATTTTTAAATAA
GAAAATTCCTTTCGGGGAAATTTC3'      (SEQ ID NO: 2)
``` or the base sequence complementary thereto or a mutation sequence thereof, wherein said primer or probe specifically detects an ovale malaria parasite under the following conditions:

(A) amplification in 100 mM Tris-HCl (pH 8.9), 1.5 mM $MgCl_2$, 80 mM KCl, 500 µg/ml BSA, 0.1% (w/v) sodium cholate, 0.1% Triton X-100, 200 µg/ml of proteinase K, 0.45% Tween 20 and 0.45% NP40 under conditions of 94° C. for 30 seconds, 50° C. for 60 seconds, and 72° C. for 60 seconds; or (B) hybridization in 5×SSC at 60° C. for 1 hour.

* * * * *